United States Patent
Keppel et al.

(10) Patent No.: US 6,389,098 B1
(45) Date of Patent: May 14, 2002

(54) DUAL MODE STEREOTACTIC LOCALIZATION METHOD AND APPLICATION

(75) Inventors: Cynthia E. Keppel, Norfolk; Fernando Jorge Barbosa, Newport News; Stanislaw Majewski, Grafton, all of VA (US)

(73) Assignee: Southeastern Universities Research Assn., Inc., Newport News, VA (US)

( * ) Notice: Subject to any disclaimer, the term of this patent is extended or adjusted under 35 U.S.C. 154(b) by 0 days.

(21) Appl. No.: 09/425,409

(22) Filed: Oct. 25, 1999

(51) Int. Cl.[7] .................................................. A61B 6/04
(52) U.S. Cl. ........................ 378/37; 378/17; 378/209; 378/98.2; 250/390.09; 250/363.02
(58) Field of Search ........................... 378/37, 17, 209, 378/98.2; 250/370.09, 363.02, 367; 5/601

(56) References Cited

U.S. PATENT DOCUMENTS 5,821,541 A * 10/1998 Tumer .................... 250/370.09
5,864,141 A * 1/1999 Majewski et al. ..... 250/363.02

* cited by examiner

Primary Examiner—Robert H. Kim
Assistant Examiner—Pamela R. Hobden

(57) ABSTRACT

The invention described herein combines the structural digital X-ray image provided by conventional stereotactic core biopsy instruments with the additional functional metabolic gamma imaging obtained with a dedicated compact gamma imaging mini-camera. Before the procedure, the patient is injected with an appropriate radiopharmaceutical. The radiopharmaceutical uptake distribution within the breast under compression in a conventional examination table expressed by the intensity of gamma emissions is obtained for comparison (co-registration) with the digital mammography (X-ray) image. This dual modality mode of operation greatly increases the functionality of existing stereotactic biopsy devices by yielding a much smaller number of false positives than would be produced using X-ray images alone. The ability to obtain both the X-ray mammographic image and the nuclear-based medicine gamma image using a single device is made possible largely through the use of a novel, small and movable gamma imaging camera that permits its incorporation into the same table or system as that currently utilized to obtain X-ray based mammographic images for localization of lesions.

7 Claims, 4 Drawing Sheets

DUAL MODE STEREOTACTIC LOCALIZATION METHOD AND APPLICATION

The United States of America may have certain rights to this invention under Management and Operating Contract DE-AC05-84ER 40150 from the United States Department of Energy.

FIELD OF THE INVENTION

The present invention relates to the field of breast lesion localization, and more particularly to a dual mode method and apparatus for localizing a breast carcinoma lesion using both nuclear medicine (scintimammography) and X-ray techniques to obtain localization results more accurate than prior art methods using only a single technique.

BACKGROUND OF THE INVENTION

X-ray mammography is the primary clinical screening tool for breast cancer. Over 15 million mammograms were performed in 1995 and over 25 million are expected to be performed by 2000. However mammography suffers from a high false positive rate. Currently, biopsies are performed following a positive mammogram to determine whether a suspicious lesion is cancerous or benign. Of the approximately 800,00 biopsies performed in 1995, roughly 600,000 were conducted on benign lesions. In addition to the expense involved, biopsy is a stressful procedure for the patient and the scarring left by the biopsy makes subsequent mammograms more difficult to interpret. Additionally, about 15–25% of all women have breast tissue that results in indeterminate mammograms. Dense tissue and scarring from prior surgery have x-ray densities similar to breast lesions, resulting in low contrast mammograms that are difficult to interpret.

Scintimammography has been shown to be able to complement mammography by imaging the metabolic activity of cancerous lesions while ignoring benign lesions and healthy tissue. In studies conducted over the past five years involving 600 women, in connection with the approval process of the DuPont Merck Pharmaceutical Company imaging agent Miraluma™, it was concluded that scintimammography is useful in differentiating cancerous and benign lesions. However, the studies also concluded that current large field-of-view gamma cameras cannot reliably image breast lesions smaller than 1.2–1.5 cm. In addition, the large size of these cameras limits their use to the lateral (side) views and does not allow for imaging the breast from other desirable viewing angles, and lesions in the chest wall are very difficult to detect.

Stereotactic breast biopsy is an X-ray guided method for localizing and sampling breast lesions discovered on mammography and considered to be suspicious for malignancy. Guided core biopsy is a relatively new procedure that has been shown to have many advantages over surgical biopsy in the form of reduced patient anticipation and discomfort. In this procedure, that is typically performed in the physician's office, the patient lies on a mammography table and the affected breast is pendantly positioned through a hole in the table in a specially designed pair of compression paddles. The physician then obtains a computerized picture of the breast and determines with varying degrees of precision the position of the suspicious breast lesion. The standard X-ray tube can be movably located perpendicular to the X-ray detector as well as +15° and −15° to the perpendicular. Localization of a specific lesion within a breast under examination is based on measurements of the position of the lesion on at least two images (a stereo pair) of the breast taken at different angles. The radiologist selects the center of the lesion, mass, or calcification and a computer generates the Cartesian coordinates of the targeted area. Once the stereo pair is generated and the computer calculates the location of the targeted area, one of several devices is employed to obtain a tissue sample for biopsy.

Further, it is well known that nuclear medicine-based gamma camera systems that rely on nuclear medicine based techniques involving the injection of a suitable radiopharmaceutical that is preferentially absorbed by cancerous tissue and detected by a gamma radiation sensitive camera device are highly more accurate in distinguishing between cancerous and benign lesions.

U.S. Pat. No. 5,595,177 to Mena et al issued Jan. 21, 1997 and U.S. Pat. No. 5,803,913 to Khalkhali et al issued Sep. 8, 1998 both disclose nuclear-medicine based apparatus, systems and methods for streotaxic localization of potential breast carcinoma lesion sites.

U.S. Pat. No. 5,289,520 to Pelligrino et al issued Feb. 22, 1994 describes a stereotactic mammography imaging table and system with X-ray projection to a CCD camera that permits detailed optical examination and analysis of the X-ray image.

None of these references discloses the combined use of an X-ray imaging device and a nuclear medicine imaging device in a single system to obtain a more accurate localization of a potentially cancerous lesion. This lack of disclosure is due to the relatively large size of both the X-ray imaging and prior art nuclear imaging or gamma camera devices that have rendered the incorporation of both such devices in a single apparatus impossible until now.

SUMMARY OF THE INVENTION

The invention described herein combines the structural digital X-ray image provided by conventional Lorad or Fischer-type stereotactic core biopsy instruments with the additional functional metabolic gamma imaging obtained with a dedicated compact gamma imaging mini-camera. Before the procedure, the patient is injected with an appropriate radiopharmaceutical, such as sestamibi (Miraluma from E. I. DuPont) or other specific breast-imaging agent. The radiopharmaceutical uptake distribution within the breast under compression in a conventional examination table expressed by the intensity of gamma emissions is obtained for comparison (co-registration) with the digital mammography (X-ray) image. This dual modality mode of operation greatly increases the functionality of existing stereotactic biopsy devices by yielding a much smaller number of false positives than would be produced using X-ray images alone. The ability to obtain both the X-ray mammographic image and the nuclear-based medicine gamma image using a single device is made possible largely through the use of a novel, small and movable gamma imaging camera that permits its incorporation into the same table or system as that currently utilized to obtain X-ray based mammographic images for localization of lesions.

DETAILED DESCRIPTION

Figure 1:
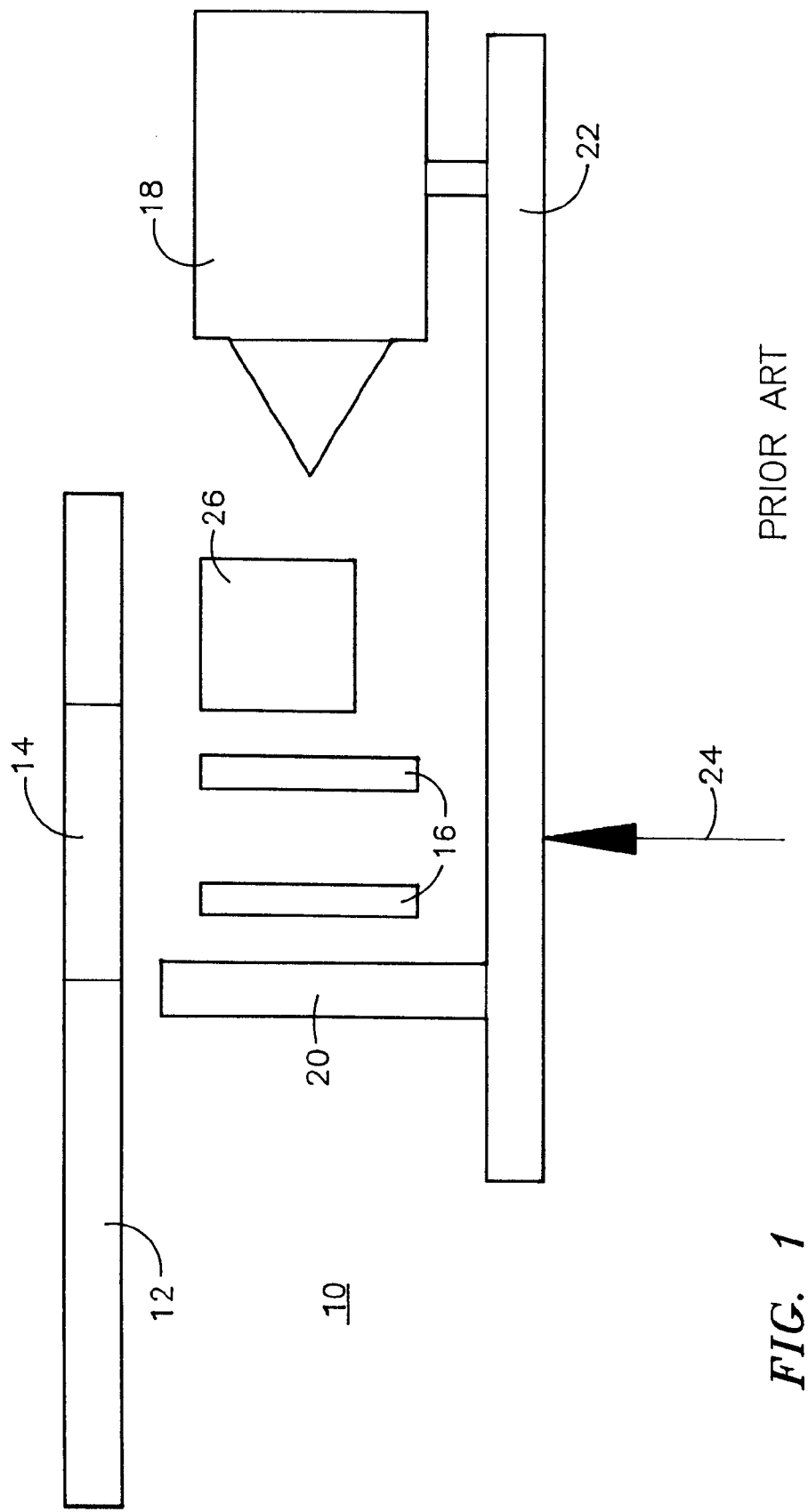
FIG. 1 is a schematic diagram of the dual mode examination device of the present invention.

Shown in schematically in FIG. 1 is a conventional arrangement for a core biopsy device. As shown in FIG. 1, examination device 10 comprises a table 12 that includes an aperture or hole 14 for pendantly accepting the female breast of a patient (not shown) lying face down on table 12. Below aperture 14 are conventional paddles 16 that receive and compress the breast under examination in the currently acceptable and used practice. An X-ray generator 18 and a digital X-ray detector 20 are mounted at opposing ends of a platform 22 that is allowed to rotate about axis of rotation 24 to permit at least two angularly displaced images (a stereo pair) to be registered in digital X-ray detector 20. All of the foregoing elements and their arrangement are well known and previously described n the prior art. In accordance with the present invention, a scintimammography, gamma sensitive mini-camera 26 (described below) is located proximate paddles 16 and in a fashion as to obtain at least two images that can be registered with those obtained by the combination of X-ray generator 18 and digital X-ray detector 20. Quite clearly, scintimammography camera 26 cannot be in position between X-ray generator 18 and digital X-ray detector 20 while X-ray images are being made so scintimammography camera 26 may either be inserted into position to acquire its registering images either just before or after the X-ray image is acquired or it to may be mounted on a platform (not shown) that rotates about axis of rotation 24 such that it can be rotated out of any obstructing position during acquisition of the X-ray images and then rotated into position to obtain its registering stereo pair of images before or after acquisition of the X-ray images. Simple mechanical mounting assures that scintimammography camera 26 is easily and reproducibly inserted or removed from position between X-ray generator 18 and X-ray detector 20. X-ray detector 20 may of course be a simple X-ray image cassette of the type conventionally used to obtain mammographic images. Location of scintimammography camera 26 may be by rotation in and out of the appropriate imaging positions, by vertical movement between these positions or even by physical removal and insertion into appropriate fittings in the under side of the examination table.

Figure 2:
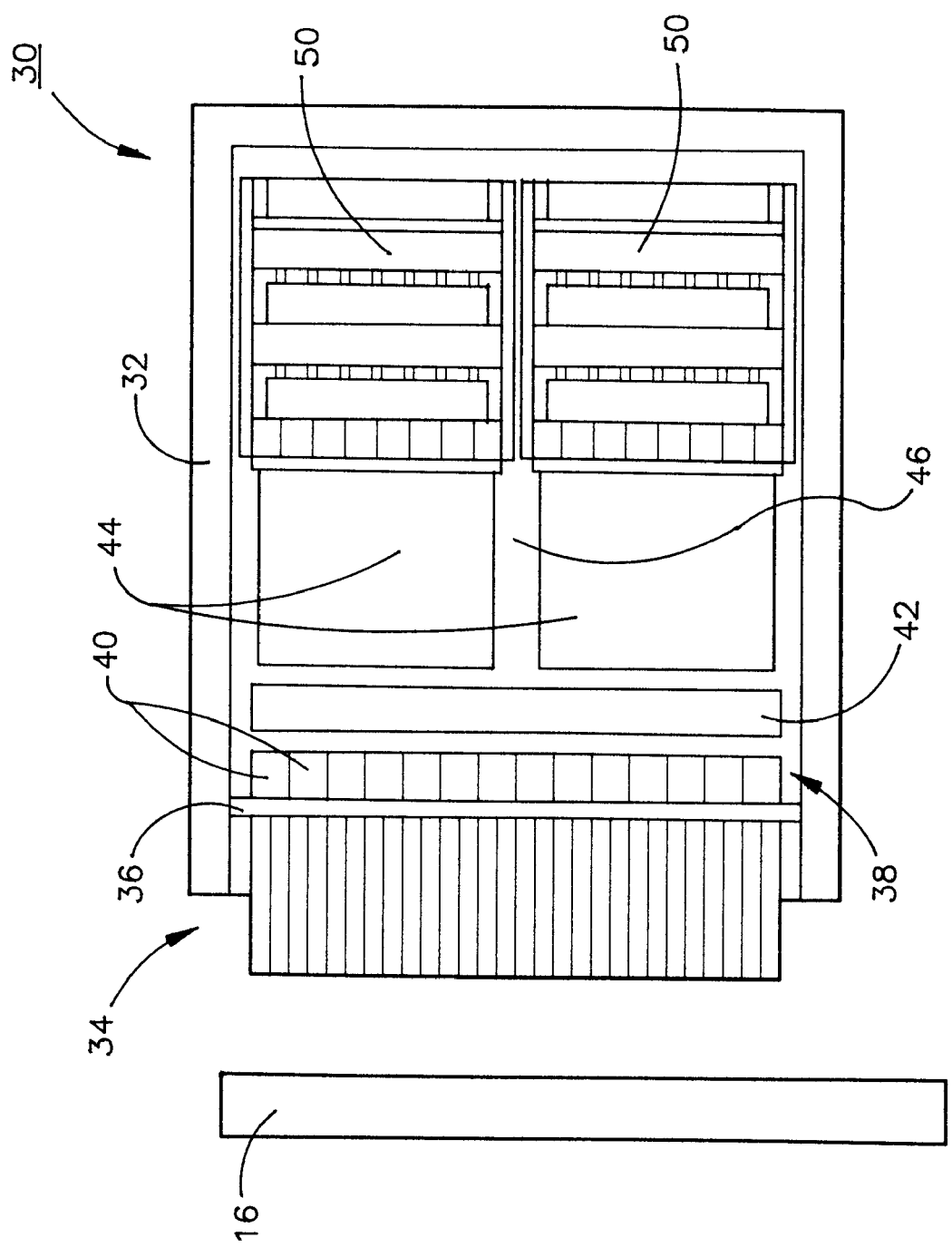
FIG. 2 is a schematic diagram of the mini gamma camera of the present invention positioned to obtain an image of a suspended breast in the device of the present invention.

The heart or core of the system of the present invention is, of course, the novel gamma camera 26 shown schematically in FIG. 2. As shown in this drawing, the camera comprises a housing 32 of machineable tungsten, lead or some other suitable material that will trap gamma rays and prevent the dissemination of stray radiation. hereinafter. Camera 26 in its operative location is positioned proximate paddle 16 as also shown in FIG. 1.

The first essential element of the camera is the collimator 34. The purpose of collimator 34, as is well known to those skilled in the art, is to align or "focus" the incoming gamma rays for their subsequent encounter with the scintillator layer. Collimator 34 of camera 26 is of any conventional design and is preferably made of etchable tungsten or lead. According to a preferred embodiment, collimator 34 is of etchable tungsten and is about 1 inch in thickness.

According to a preferred embodiment, immediately behind or separated by a small air gap (on the order of 0.010") is a layer 36 of a light impermeable material such as a thin foil of aluminum. A principal purpose of optional layer 36 is to insure that no extraneous light enters the camera and impinges upon the scintillator or the photomultiplier tubes described below. The presence of such stray radiation could, of course, affect any subsequent images produced by the camera. A secondary purpose of layer 36 is to serve to protect the friable scintillator layer 38 from physical damage. According to a preferred embodiment, layer 36 is made of aluminum and is about 0.04" thick.

Behind layer 36 is scintillator layer 38. Scintillator layer 38 may be contiguous with layer 36 or separated therefrom by thin protective compressed foam layer (not shown). When present, the compressed foam layer serves to cushion or protect the friable scintillator layer 38 from physical damage through shock. Scintillator layer 38 comprises a scintillator array comprising individual 2–4 mm side dimension and 3–10 mm length dimension scintillator pixels 40. Individual scintillator pixels 40 may be of any conventional scintillator crystal that will produce adequate response to the required incoming dosage of gamma radiation, and such scintillator materials, their design and fabrication are well known in the art. Some examples of useful scintillators are CeI(TI), CeI(Na), NaI(TI), YAP, YSO, GSO, LSO and LGSO. According to a preferred embodiment of the present invention, scintillator array 38 is comprised of individual 3×3×3 mm CeI (Na) pixels with an overall outside dimension of about 52.5×52.5 mm which matches very well the conventional X-ray image size. According to a further preferred embodiment, scintillator array 38 is coated with a layer of bonding material such as aluminum oxide in an epoxy matrix (not shown). The selection of the scintillator and any coating is, of course, a matter of choice well within the capabilities of the skilled artisan, and is not critical to the successful practice of the present invention. Adjacent behind scintillator layer 38 is light guide 42. Light guide 42 serves to conduct the visible light produced by scintillator layer 38 in response to incoming gamma radiation to underlying photomultiplier array 44. As the visible light is conducted, it is diffused somewhat. This phenomenon is known in the art, and is used to "mask" so-called dead space that occurs at the edges of any adjacent photomultiplier moduless in array 42. Conventionally, light guides of this type are made of glass, however, we have discovered that a simple and inexpensive acrylic material works equally well. Hence, according to a preferred embodiment of the present invention, light guide 42 is made of acrylic and has a thickness of about 3/16".

Figure 3:
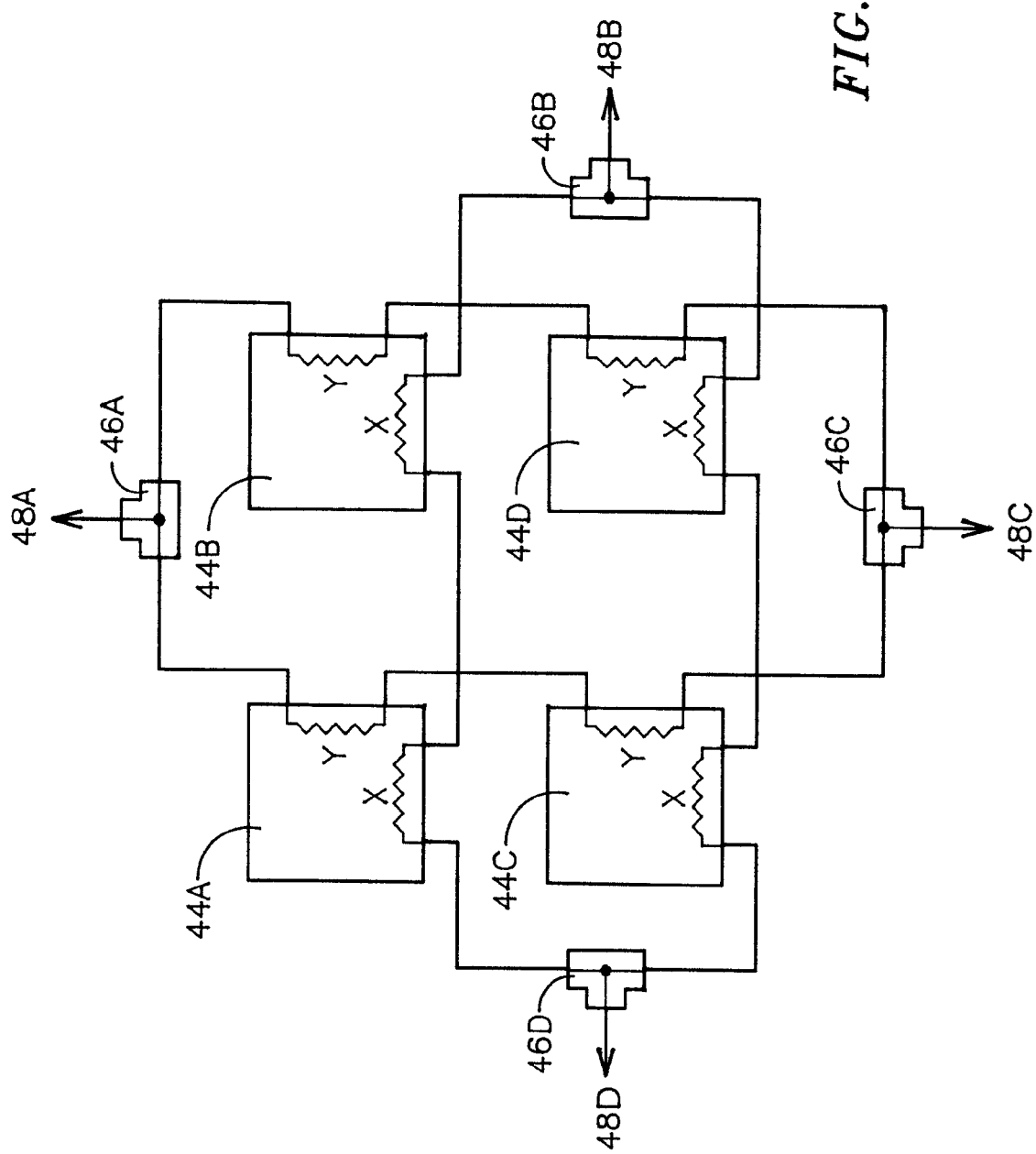
FIG. 3 is a schematic diagram of the circuitry used to generate spatial orientation information from the photomultiplier tubes used in the scintillation camera of the present invention.
Figure 5:
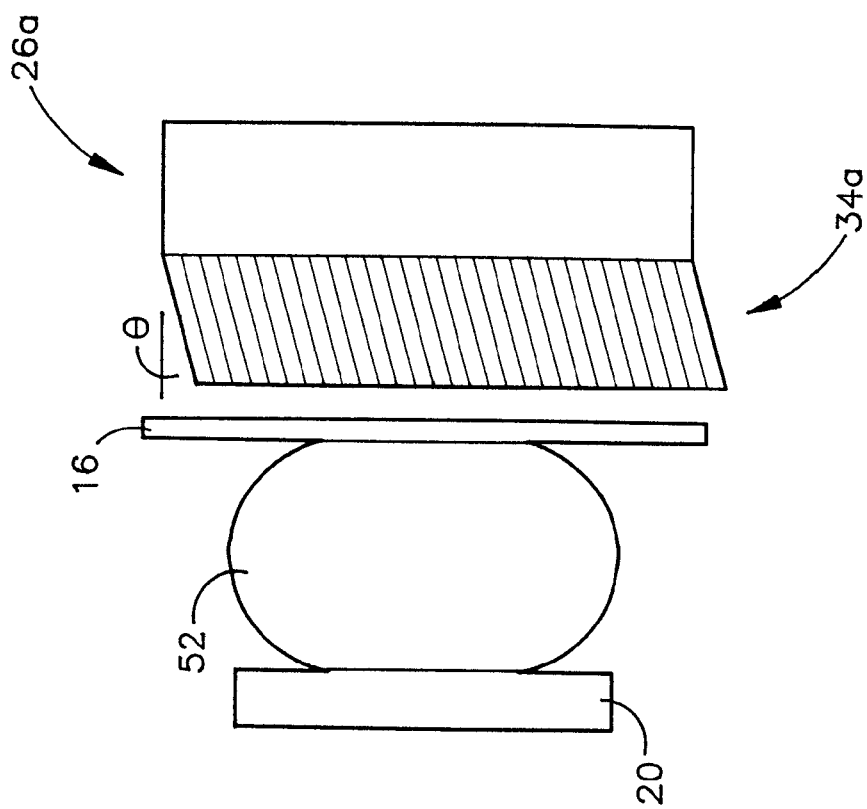

A critical element of the present invention resides in photomultiplier module array 44 that lies behind scintillator layer 38. Photomultiplier module array 44 consists of an assembly of four generally rectangular individual, position sensitive, high-resolution photomultipliers. In the case of a preferred embodiment, each of the individual photomultiplier modules 44 is about one inch square. Each single photomultiplier module uses the resistive network shown in FIG. 3 to read eight individual anodes (4x and 4y) of the individual photomultipliers and convert them into four outputs for further processing. The electronic outputs of the individual modules are connected as shown schematically in FIG. 3 to form an approximate 2"×2" scintillation light sensor. The use of a matrix of four such photomultipliers provides an approximately 4"×4" image that approximates the size of the image produced using the X-ray mammography system.

The preferred photomultiplier device for use in scintillation camera 30 is a Model R7900-C8 produced by Hamamatsu Photonics K.K., 314-5 Shimokanzo, Toyooka Village, Iwata-qun, Shizuoka-ken, 438-0193 Japan. These photomultiplier units are about 30 mm square and demonstrate an effective area about 22 mm square. Their spectral response is in the range of 300 to 650 nm with a peak wavelength of 420 nm. Preferably, between each of the individual photomultipliers 44 is a thin layer 46 of aluminum oxide in an epoxy matrix similar to that preferably coated over photomultiplier array 38. Thin layer 46 serves as the binder which holds photomultipliers 44 together and also serves to reflect light which impinges this joint area back toward the appropriate photomultiplier 44 so that no available photons are absorbed or lost in the system.

Behind each of photomultipliers 44 are of high voltage supplies and amplifiers 50 each individually connected to a photomultiplier 44. When connected as described below, this electronic circuitry provides to an appropriate computing device (not shown) the digitized information and signals necessary to obtain the image and spatial location information required to determine the size, character and location of any lesion that may be present.

Figure 4:
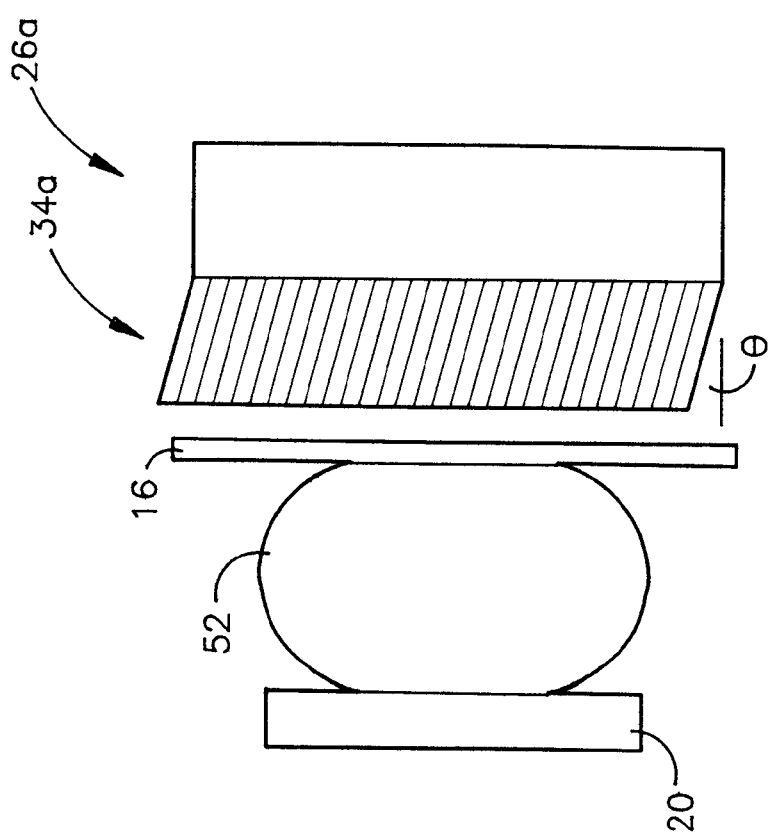

Each of individual photomultipliers 44, i.e. 44A, 44B, 44C and 44D are connected as shown in FIG. 4 to provide via splitter/combiners 46A, 46B, 46C and 46D individual outputs 48A, 48B, 48C and 48D which provide spatial orientation of signals generated by the individual photomultipliers.

The scintimammography camera of the present invention provides a spatial resolution on the order of about 2 mm as opposed to one half or more centimeters as was obtainable with either X-ray or prior art, gamma sensitive cameras. This combined with the ability to place the camera in close proximity to the breast as shown in FIGS. 1 and 2 all serve to increase small lesion sensitivity and localization capability.

In use, the patient undergoing examination is first injected with a suitable radiopharmaceutical, placed on above described examination table 12 with one breast extending through aperture 14, paddles 16 compressed about said breast in the conventional fashion, and a stereo pair of X-ray images acquired in the conventional manner while scintimammography camera 26 is move out of the field of view of X-ray detector 20. Scintimammography camera 26 is then moved into position as shown in FIG. 2 and an identical stereo pair of images acquired therewith. The digital X-ray images are then registered electronically with the digital scintimammography images and any lesions and their location positively located. Because of the higher malignancy determination capability of the scintmammography camera better decisions can be made as to whether a biopsy by any conventional method is required.

As the invention has been described, it will be apparent to those skilled in the art that the same may be varied in many ways without departing from the spirit and scope of the invention. Any and all such modifications are intended to be included within the scope of the appended claims.

What is claimed is:

1. In a mammographic examination system comprising:
   A) a table;
   B) an aperture in said table to receive the breast of a female patient lying on said table;
   C) a pair of paddles below said aperture oriented to compress said breast for purposes of mammographic examination; and
   D) an X-ray generator and an X-ray detector movably located below said table and providing the ability to produce a stereo pair of X-ray images of said breast: the improvement comprising the incorporation of a movable scintimammography camera that is removed from the field of view of said X-ray detector when said stereo pair of X-ray images is being produced and placed in proximity with said paddles to provide a stereo pair of scintimammography images that can be registered with said stereo pair of X-ray images to provide a dual mode stereotactic localization apparatus.

2. The dual mode stereotactic localization apparatus of claim 1 wherein said X-ray generator and said X-ray detector are mounted on a rotatable support arm.

3. The dual mode stereotactic localization apparatus of claim 1 wherein said scintimammography camera comprises:

A) a collimator;
   B) behind said collimator a scintillator array positioned to receive gamma radiation from said collimator;
   C) a light guide positioned to receive visible light emitted by said scintillator array and transmit it to;
   D) an array of photomultiplier modules each individually connected to;
   E) a resistive electronic circuit comprising a high voltage supply and an amplifier for generation of a digital image.

4. The dual mode stereotactic localization apparatus of claim 3 wherein said array of photomultiplier modules comprises a two by two, square array of four photomultiplier modules.

5. The dual mode stereotactic localization apparatus of claim 4 wherein said array of photomultiplier modules measures about 4"×4".

6. The dual mode stereotactic localization apparatus of claim 4 wherein said scintillator is selected from the group consisting of CeI(TI), CeI(Na), NaI(TI), YAP, YSO, GSO, LSO and LGSO.

7. A dual mode method for the stereotactic localization of potentially cancerous lesions comprising the steps of:

A) injecting a patient to subjected to examination with a suitable radiopharmaceutical;
   B) placing said patient face down on a dual mode stereotactic examination device comprising:
      1) a table;
      2) an aperture in said table to receive the breast of said female patient;
      3) a pair of paddles below said aperture oriented to compress said breast for purposes of mammographic examination;
      4) an X-ray generator and an X-ray detector movably located below said table and providing the ability to produce a stereo pair of X-ray images of said breast; and
      5) a scintimammography camera also mounted below said table that is removed from the field of view of the X-ray detector when said stereo pair of X-ray images is being acquired and placed in proximity with said paddles to provide a stereo pair of scintimammography images;

C) producing said stereo pair of X-ray images of said breast by exposing said X-ray detector to X-rays produced by said X-ray generator through said breast from two different positions while said moveable scintimammography camera is out of the field of view of said X-ray detector;

D) placing said scintimmamography camera in proximity with said paddles;

E) producing a stereo pair of images with said scintimammography camera by exposing said breast to said scintimammography camera from said two different positions; and F) registering said X-ray stereo pair of images and said scintimammography camera stereo pair of images.

* * * * *